(12) United States Patent
Slaugh et al.

(10) Patent No.: US 6,559,349 B1
(45) Date of Patent: *May 6, 2003

(54) PROCESS FOR SEPARATING INTERNAL AND ALPHA OLEFINS FROM SATURATED COMPOUNDS

(75) Inventors: Lynn Henry Slaugh, Houston, TX (US); Howard Lam-Ho Fong, Sugar Land, TX (US); Laurent Alain Fenouil, Houston, TX (US)

(73) Assignee: Shell Oil Company, Houston, TX (US)

( * ) Notice: Subject to any disclaimer, the term of this patent is extended or adjusted under 35 U.S.C. 154(b) by 2 days.

This patent is subject to a terminal disclaimer.

(21) Appl. No.: 09/722,843

(22) Filed: Nov. 27, 2000

Related U.S. Application Data

(62) Division of application No. 09/379,089, filed on Aug. 23, 1999, now Pat. No. 6,184,431.

(51) Int. Cl.[7] .............................. C07C 7/00; C07C 7/10
(52) U.S. Cl. ..................... 585/867; 585/865; 585/833; 585/804
(58) Field of Search ............................. 585/867, 865, 585/833, 804

(56) References Cited

U.S. PATENT DOCUMENTS

| | | | |
|---|---|---|---|
| 2,775,633 A | 12/1956 | Fenske et al. | 260/677 |
| 2,953,611 A | 9/1960 | Spengler | 260/677 |
| 3,306,946 A | 2/1967 | Snyder et al. | 260/677 |
| 3,444,261 A | 5/1969 | Caprioli et al. | 260/683 |
| 3,534,116 A | 10/1970 | Fuller | 260/674 |
| 3,674,885 A * | 7/1972 | Griesinger et al. | 208/950 |
| 3,864,420 A | 2/1975 | Dombro | 260/677 A |
| 4,710,273 A | 12/1987 | Okamoto | 203/29 |
| 4,915,794 A | 4/1990 | Slaugh et al. | 203/29 |
| 4,946,560 A | 8/1990 | Slaugh et al. | 203/38 |
| 5,012,034 A | 4/1991 | Weingaertner et al. | 585/806 |
| 5,811,623 A * | 9/1998 | Ryu et al. | 585/316 |
| 5,936,136 A | 8/1999 | Slaugh et al. | 585/867 |
| 5,942,656 A | 8/1999 | Slaugh et al. | 585/864 |
| 6,018,089 A | 1/2000 | Slaugh et al. | 585/867 |
| 6,184,431 B1 * | 2/2001 | Slaugh et al. | 585/25 |
| 6,211,423 B1 * | 4/2001 | Slaugh et al. | 585/804 |

OTHER PUBLICATIONS

U.S. patent application Ser. No. 08/987,554, Slaugh et al., filed Dec. 9, 1997, (now issued) 6,018,089.
U.S. patent application Ser. No. 09/309,417, Slaugh et al., filed May 11, 1999.
U.S. patent application Ser. No. 09/379,223, Slaugh et al., filed Aug. 23, 1999.
U.S. patent application Ser. No. 09/379,090, Slaugh et al., filed Aug. 23, 1999.

* cited by examiner

Primary Examiner—Walter D. Griffin
Assistant Examiner—Tam M. Nguyen

(57) ABSTRACT

A process for separating and isolating saturated hydrocarbons from olefins, and in particular, a process for separating and isolating saturated hydrocarbons from olefins in a Fisher-Tropsch stream. The feedstock composition is contacted with linear polyaromatic compound under conditions effective to form linear polyaromatic compound-olefin adducts. Separation of the adducts from the stream also separates the adducted olefins from the stream. After dissociation of the adducted olefins, the process results in an olefin composition that is enriched in concentration of olefins over the concentration of olefins in the feedstock composition, and a saturated hydrocarbon stream that is enriched in saturated hydrocarbons over the concentration of saturated hydrocarbons in the feedstock.

150 Claims, 1 Drawing Sheet

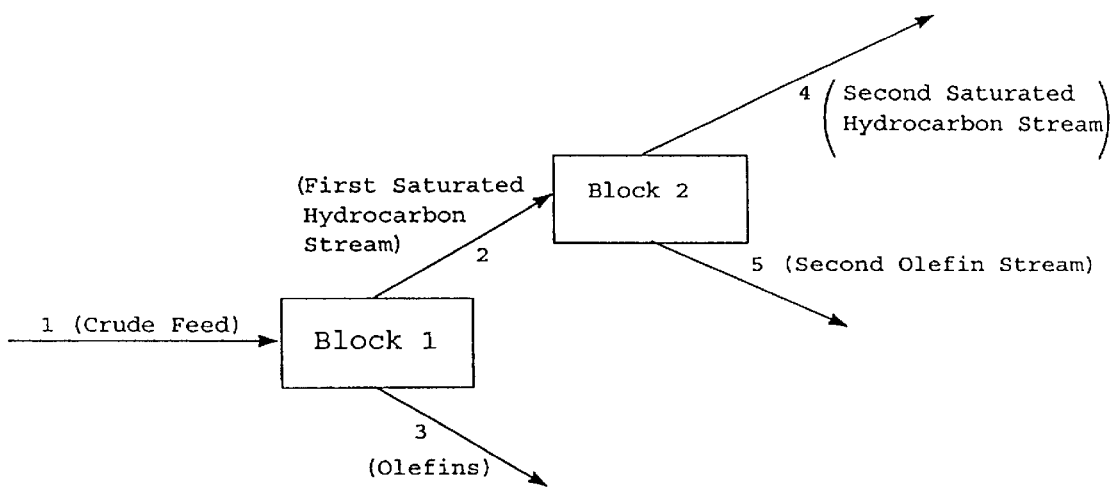

US 6,559,349 B1

PROCESS FOR SEPARATING INTERNAL AND ALPHA OLEFINS FROM SATURATED COMPOUNDS

This is a division of application Ser. 09/379,089 filed Aug. 23, 1999, now U.S. Pat. No. 6,184,431 the entire disclosure of which is hereby incorporated by reference.

1. FIELD OF THE INVENTION

This invention relates to a process for separating olefins from saturated hydrocarbons followed by separating linear alpha olefins and internal olefins from a saturated hydrocarbon stream.

2. BACKGROUD OF THE INVENTION

Many industrial processes produce olefin/saturated hydrocarbon streams that are mixtures of olefins, saturated hydrocarbons, and oxygenates. Olefins are frequently used in the manufacture of polymers such as polyethylene, as drilling mud additives, or as intermediates for the production of oil additives and detergents. Some industrial processes manufacture olefin streams by oligomerizing ethylene over an alpha olefin catalyst to produce mixtures of alpha and internal olefins having a broad range of carbon numbers. However, these streams rely on the use of ethylene as a feedstock material, which add a significant cost to the manufacture of the olefin. On the other hand, the FT process starts with an inexpensive feedstock, syngas, generally derived from natural gas, coal, coke, and other carbonaceous compounds to make oligomers comprised of olefins, aromatics, saturates, and oxygenates.

The FT process, however, is not very selective to the production of olefins. While reaction conditions and catalysts can be tuned to manufacture a stream rich in the desired species within the FT product stream, a large percentage of the FT stream contains other types of compounds which must be separated from the olefins, which olefins are purified, and then sold into different markets. For example, a typical commercial FT stream will contain a mixture of saturated hydrocarbons, olefins, aromatics, and oxygenates such as organic carboxylic acids, alcohols, ethers, esters, ketones, and aldehydes. All these compounds must be separated from the crude FT stream before a particular composition may be offered commercially. To further complicate the separation operation, the FT stream contains compounds having a wide spectrum of carbon numbers, as well as a wide variety of olefins, ranging from $C_2$–$C_{200}$ species, internal linear olefins, alpha linear olefins, internal branched olefins, alpha branched olefins, and cyclic olefins, many of which have similar molecular weights. Separating and isolating these species is no easy task. Conventional distillation methods are frequently inadequate to separate species having closely related boiling points.

Various processes have been proposed to efficiently separate the different species in an FT stream with sufficient purity that a particular composition is acceptable in the intended application. These processes for separating out different species in an FT stream include the use of molecular sieves, which are restricted to a feed have an average carbon number range which is more limited than a composition containing a broad spectrum of average carbon numbers ranging from $C_5$–$C_{20}$, to the use of exchange resins, to the use of super-fractionators often operated at high pressure, and the use of oligomerization catalysts or etherification techniques to alter the boiling points of the species in the FT stream. Many reactive methods for separating species in an FT stream do not, however, selectively react with olefins while simultaneously reject paraffins.

U.S. Pat. No. 4,946,560 described a process for the separation of internal olefins from alpha olefins by contacting a feedstock with an adducting compound such as anthracene to form an olefin adduct, separating the adduct from the feedstock, dissociating the olefin adduct through heat to produce anthracene and an olefin composition enriched in alpha olefin, and separating out the anthracene from the alpha olefin. This reference does not suggest the desirability or the capability of anthracene to separate olefins from saturated hydrocarbons or linear alpha olefins from saturated hydrocarbons.

Once olefins are separated from saturated hydrocarbons, it would also be desirable to purify the removed saturated hydrocarbons and extract as much remaining olefin from the removed saturated hydrocarbon as possible.

3. SUMMARY OF THE INVENTION

This invention relates to a process for separating olefins from saturated hydrocarbons, and thereafter further treating the olefins to separate olefins from a stream of saturated hydrocarbons. The process of the invention is well suited to treating a FT stream.

In particular, there is provided a process for treating a feedstock composition comprising linear alpha olefins, internal olefins, and saturated hydrocarbons, comprising:

a) contacting the feedstock composition with a linear polyaromatic compound in a first reaction zone under conditions effective to form a reaction mixture comprising linear polyaromatic compound-olefin adducts and saturated hydrocarbons;

b) separating the first linear polyaromatic compound-olefin adducts from the saturated hydrocarbons in the reaction mixture to form an adducted olefin stream and a first saturated hydrocarbon stream enriched in the concentration of saturated hydrocarbons over the concentration of saturated hydrocarbons in the feedstock composition;

si) contacting the saturated hydrocarbon stream with a linear polyaromatic compound in a second reaction zone under conditions effective to form a reaction mixture comprising second linear polyaromatic compound-olefin adducts and saturated hydrocarbons;

sii) separating the second linear polyaromatic compound-olefin adducts from the saturated hydrocarbons in the reaction mixture to form a second adducted olefin stream comprising the second linear polyaromatic compound-olefin adducts, and a second saturated hydrocarbon stream enriched in the concentration of saturated hydrocarbons over the concentration of saturated hydrocarbons in the first saturated hydrocarbon stream;

siii) dissociating the second linear polyaromatic compound-olefin adducts to form linear polyaromatic compounds and a second olefin composition comprising alpha olefins and internal olefins enriched in the concentration of alpha olefins and internal olefins over each of their concentrations in the first saturated hydrocarbon stream.

4. BRIEF DESCRIPTION OF THE DRAWINGS

The FIGURE is a block flow diagram representing the process of adducting and separating a crude feedstream of olefin and saturated hydrocarbon and subjecting the separated saturated hydrocarbon stream to a further adducting/separation/dissociation treatment to further separate internal and linear alpha olefins from the saturated hydrocarbon stream.

5. DETAILED DESCRIPTION OF THE INVENTION

As used throughout this specification and in the claims, the term "comprising" means "at least," such that other unmentioned elements, ingredients, or species are not excluded from the scope of invention.

The feed stream to be treated comprises at least olefins and saturated hydrocarbons. The class of saturated hydrocarbons as used herein includes at least a paraffin. The class of saturated hydrocarbons may also include other molecules such as cycloparaffins.

An olefin means any compound containing at least one carbon-carbon double bond. The olefins may be linear, branched, conjugated, contain multiple double bonds anywhere along the chain, substituted, unsubstituted, contain aryl or alicyclic groups, or contain heteroatoms.

The olefins may contain aryl moieties along with an aliphatic or cycloaliphatic moiety within the same compound, or may consist solely of an aliphatic, cycloaliphatic, or cycloaliphatic with aliphatic moieties on the compound. Preferably, the olefin is an aliphatic compound.

The olefin may be branched or linear. Examples of branching include alkyl, aryl, or alicyclic branches. The number of unsaturation points along the chain is also not limited. The olefin may be a mono-, di-, tri-, etc. unsaturated olefin, optionally conjugated. The olefin may also contain acetylenic unsaturation.

An alpha olefin is an olefin whose double bond is located on both of $\alpha$ and $\beta$ carbon atoms. An $\alpha$ Carbon atom is any terminal carbon atom, regardless of how long the chain is relative to other chain lengths in a molecule. The alpha olefin may be linear or branched. Branches or functional groups may be located on double bond carbon atoms, on carbon atoms adjacent to the double bond carbon atoms, or anywhere else along the carbon backbone. The alpha olefin may also be a polyene, wherein two or more points of unsaturation may be located anywhere along the molecule, so long as at least on double bond is in the alpha position.

An internal olefin(s) is an olefin whose double bond is located anywhere along the carbon chain except at any terminal carbon atom. The internal olefin may be linear or branched. The location of a branch or substitution on the internal olefin is not limited. Branches or functional groups may be located on the double bond carbon atoms, on carbon atoms adjacent to the double bond carbon atoms, or anywhere else along the carbon backbone.

The olefin may also be substituted with chemically reactive functional groups. These types of compounds are identified as oxygenates. Examples of chemically reactive functional groups are carboxyl, aldehyde, keto, thio, ether, hydroxyl, and amine. The number of functional groups on a molecule is not limited. The functional groups may be located anywhere along the carbon backbone.

The feedstock is generally produced by commercial processes such as the oligomerization of ethylene, optionally followed by isomerization and disproportionation. Alternatively, the feedstock may be produced by the Fisher-Tropsch process, which typically contains a high proportion of paraffins. A Fisher-Tropsch process catalytically hydrogenates CO to produce compositions containing aliphatic molecular chains. Other processes for making feedstocks which may contain mixtures of olefins and paraffins include the dehydrogenation of paraffin, such as those made by the Pacol™ processes of UOP, and the cracking of waxes. The most preferred feedstock is that obtained from a Fisher-Tropsch (FT) synthesis.

FT catalysts and reaction conditions can be selected to provide a particular mix of species in the reaction product stream. For example, the particular catalyst and reaction conditions may be tuned to enhance the amount of olefins and decrease the amount of paraffins and oxygenates in the stream. Alternatively, the catalyst and reaction conditions may be tuned to enhance the amount of paraffins and decrease the amount of olefins and oxygenates in the stream.

Generally, the reaction conditions will vary depending on the type of equipment employed. The FT reaction temperatures vary between 100° C. to 500° C., an inlet gas pressure to the reactor from atmospheric to 1500 psig, and an $H_2/CO$ ratio from 0.5:1 to 5:1, preferably from 1.8:1 to 2.2:1, and gas hourly space velocity ranging from 1 to 10,000 v/v/hour. A variety of reactor vessel configurations can be used, including a fluidized(entrained) bed, a fixed bed, and a slurried bed. The temperature in these beds can be adjusted by those of ordinary skill to optimize the formation of FT products, including hydrocarbons, and particularly, olefins and types of olefins. To illustrate without limitation, in fluidized (entrained) bed(s), the temperature of reaction is generally high—e.g. ranging from 280° to 350° C., preferably 310° to 340° C. If a fixed bed reactor(s) is used, the reaction temperature is generally ranges within 200° C. to 200° C., preferably between 210° and 240° C., and when a slurry bed reactor(s) is used, the temperature is generally within the range of 190° C. to 270° C.

The catalyst used in the FT process is any known in the art, but preferably from among Mo, W, and Group VIII compounds, including iron, cobalt, ruthenium, rhodium, platinum, palladium, iridium, osmium, combinations of the foregoing, combinations with other metals, and each being in the free metal form or as alloys, or as an oxide or carbide or other compound, or as a salt. Iron based and cobalt based catalysts have found common commercial use, and ruthenium has gained importance as a metal for the catalyst which favors the formation of high melting waxy species under high pressure conditions. Those of skill in the art recognize which catalysts and combinations will favor the manufacture of desired species in the FT reaction composition. For example, fused iron containing a promoter such as potassium or oxides on a silica, alumina, or silica-alumina support are known as FT synthetic catalysts. Another example is the use of Co metal. Cobalt has the advantage of producing less methane during synthesis over the older nickel based catalysts, and produces a wide spectrum of species. With the proper selection of supports, promoters, and other metal combinations, the cobalt catalyst can be tuned to manufacture a composition rich in the desired species. Other catalysts, such as iron-cobalt alloy catalysts, are known for their selectivity toward olefins under certain process conditions.

The catalysts may be fused or precipitated, or sintered, cemented, impregnated, kneading or melting onto a suitable support.

The catalysts may also contain promoters to promote the catalyst's activity, stability, or selectivity. Suitable promoters include alkali or alkaline earth metals, in free or combined form as an oxide, hydroxide, salt, or combinations thereof.

An FT stream generally contains virtually no sulfur or nitrogen compounds, which may be deleterious to other catalysts which derivatize the olefins or catalyze the reaction of olefins in other oligomerization or polymerization processes. Regardless of the method used, however, the FT process is not very selective to a particular species, and yields a wide variety of species within a composition.

Examples of some of the species found in any FT stream include paraffins having a broad spectrum of molecular weights, alcohols, acids, ketones, and aldehydes, and small amounts of aromatics. The linear polyaromatic compound used in the process of the invention, however, is particularly well adapted for the separation of olefins from saturated hydrocarbons in an FT stream in the presence of oxygenates since oxygenates do not significantly impair the performance of the linear polyaromatic compound.

While reference is made to a FT stream, it is to be understood that any stream made by any process containing olefins and saturated hydrocarbons are suitable feedstocks for the process of the invention. Most crude FT streams contain from 5% to 95% olefins, the remainder being saturated hydrocarbons comprising paraffins and cycloparaffins, and optionally other compounds such as aromatics optionally containing saturated or unsaturated alkyl branches, and oxygenates, based on the weight of all ingredients in the feedstock stream to the process of the invention. The preferred amount of olefin present in the FT stream ranges from 15 wt. % to 70 wt. %, based on the weight of the FT stream. The amount of linear alpha olefin in the FT stream is not limited, but preferably ranges from 15 wt. % to 65 wt. %, based on the weight of the FT stream. The amount of other olefins, including branched olefins and internal olefins, both linear and branched, is also not limited, but preferably ranges from 1 wt. % to 55 wt. %, more typically from 5 wt. % to 45 wt. %, based on the weight of the FT stream. The amount of paraffin in most FT streams range from 5 wt. % to 99 wt. %. In some FT streams, the FT catalyst is tuned to enhance the olefin concentration and decrease the paraffin concentration. In these streams, the amount of paraffin generally ranges from 5 to 65 wt. % of the stream. In other FT streams where the FT catalyst is tuned to enhance the amount of paraffin, the amount of paraffin in the stream ranges from 65 wt. % to 99 wt. %. The amounts of other compounds in a FT stream, such as oxygenates and aromatics, make up most of the remainder of the FT stream, and are generally present in amounts ranging from 5 wt. % to 40 wt. %. Minor amounts of other by-products and impurities, less than 5 wt. %, may be present in most FT streams. An FT stream which consists essentially of paraffins, olefins, aromatics and oxygenates can include such minor amounts of other by-products and impurities.

The feedstock may be a processed FT stream which has been fractionated and/or purified by a conventional distillation, extraction, or other separation operation to obtain a desired carbon number cut, including a composition containing a mixture of carbon numbers or a single carbon cut composition, and to remove high and low boiling compounds, including olefins, paraffins, aromatics, and oxygenates from the crude stream. When the separation operation is conducted by distilling the reaction mixture containing the adduct, it is preferred that the feedstock used in the process of the invention contain an average carbon number ranging from $C_5$–$C_{20}$ and wherein the predominant olefin species in the feedstock is within the range of $C_5$–$C_{20}$, inclusive. The polyaromatic adducting compound efficiently separates the saturated hydrocarbons from the olefins when the average carbon number of the feedstock and the predominant olefinic species is within this range, inclusive. When the average carbon number of the feedstock exceeds $C_{20}$, the polyaromatic compound-olefin adduct boils at a lower temperature than many of the species in the $C_{20}+$ feedstock composition, thereby leaving these high boiling species in the reaction mixture bottoms containing the adduct. Accordingly, the particular polyaromatic compound and the particular feedstock composition should be so selected that the polyaromatic compound-olefin adduct composition in the reaction mixture boils at a higher temperature than the amount of unreacted paraffin species in the feedstock one desires to separate. Therefore, in this preferred embodiment, the feedstock stream is one which contains an average carbon number ranging from $C_5$–$C_{20}$, and more preferably ranging from $C_6$–$C_{18}$, and wherein the predominant olefin species is within these ranges, inclusive. These types of FT streams are generally processed by one of the techniques identified above to substantially remove cuts containing ingredients below or exceeding the range of $C_5$–$C_{20}$.

In addition to mixtures of olefins within this range, one may also employ what are known as single carbon cuts of olefins as feedstocks, wherein the single cut is within this range. For example, the feedstock employed may be a single $C_6$, $C_8$, $C_9$, $C_{10}$, $C_{11}$, $C_{12}$, $C_{14}$, or $C_{16}$ carbon cut. These carbon cuts have utility as comonomers for polyethylene, PAO, alpha olefin sulfonates, and as drilling fluids.

In the event that one desires to employ a feedstock outside of the range of $C_5$–$C_{20}$, other separation techniques can be used to separate the adduct from the unreacted reaction mixture, including the selection of higher boiling polyaromatic compounds and/or other separation techniques such as liquid/liquid extraction or crystallization. These techniques, of course, can also be used with feedstocks within the range of $C_5$–$C_{20}$, inclusive.

The linear polyaromatic compound is utilized in the instant process to form the adduct with the olefins in the feed stream. As used herein, "linear polyaromatic compound" refers to a linear polyaromatic compound having at least three fused aromatic rings, which may be unsubstituted or substituted and possess similar adducting properties as the unsubstituted molecule, and mixtures thereof. The linearity should extend to at all three of the fused rings if a three fused ring compound is used and to at least four consecutively fused cyclic rings if a four or more fused ring compound is used. The linear polyaromatic compound also refers to mixtures of compounds containing as one of their ingredients the linear polyaromatic compound, including but not limited to coal tars, anthracene oil, and any crude mixtures containing cuts separated from naphthalene. The linear polyaromatic compound also includes aromatic molecules linked together by a bridging group, such as a hydrocarbon chain, an ether linkage, or a ketone group containing chain so long as at least three fused rings are present in a linear arrangement; as well as those containing a heteroatom which do not interfere in the separation of olefins from saturated hydrocarbons.

The linear polyaromatic compound has a preferential selectivity toward adducting with linear alpha olefin compounds, and secondly with other olefins, and last with paraffins, with which the compound is virtually unreactive under any operating condition outside of cracking conditions. The linear polyaromatic compound of choice is one which has a selectivity for linear alpha olefin compounds over other olefins greater than 1:1 by mole, preferably 2:1 or more, more preferably 4:1.

Non-limiting examples of the linear polyaromatic compound include anthracene, 2,3-benzanthracene, pentacene, and hexacene. Suitable examples of substituents on substituted linear polyaromatic compounds include, but are not limited to, lower alkyl, e.g., methyl, ethyl, butyl; halo, e.g., chloro, bromo, fluoro; nitro; sulfato; sulfonyloxy; carboxyl; carbo-lower-alkoxy, e.g., carbomethoxy, carbethoxy; amino; mono- and di-lower-alkylamino, e.g., methylamino, dimethylamino, methylethylamino; amido; hydroxy; cyano; lower-alkoxy, e.g., methoxy, ethoxy; lower-alkyanoyloxy, e.g., acteoxy; monocyclic aryls, e.g., phenyl, xylyl, toluyl, benzyl, etc. The particular substituent size, their number, and their location, should be selected so that they are relatively inert under the reaction conditions and not so large as to block the formation of the Diels-Alder adduct. Suitable substituted linear polyaromatic compounds can be determined by routine experimentation. Examples of suitable linear polyaromatic compounds include 9,10-dimethylanthracene, 9,10-dichloroanthracene, 9-methylanthracene, 9-acetylanthracene, 9-(methylaminomethyl)anthracene, 2-choloranthracene, 2-ethyl-9,10-dimethoxyanthracene, anthrarobin, and 9-anthryl trifluoromethyl ketone. The preferred linear polyaromatic compounds are anthracene and 2,3-benzanthracene.

In a first reaction zone in step a), the feedstock composition, preferably an FT feedstock stream having an average carbon number ranging from $C_6$–$C_{18}$, is contacted with a linear polyaromatic compound. In the second reaction zone, the saturated hydrocarbon stream removed from the first reaction zone is also contacted with a linear polyaromatic compound. In each reaction zone, the Diels-Alder adduct forming reaction is carried out in a conventional fashion. Examples of suitable equipment in which the reactions are carried out include a continuously stirred tank reactor, configured as a single unit, in parallel, or in series, wherein feedstock or an olefin composition, and linear polyaromatic compound, are added continuously to a stirred tank to form a liquid reaction mixture under heat, and the reaction mixture is continuously withdrawn from the stirred tank. Alternatively, the reaction may be carried out in a bubble column, or in a batch reactor, or utilizing a plug flow reaction scheme. The feedstock and olefin composition adducting reactions are typically carried out over a range of temperatures from about 150° to about 290° C., preferably from about 200° to about 280° C., and most preferably from about 240° to about 265° C. Pressures typically run from about atmospheric to about 100 atmospheres. The reactions can be carried out in the gas phase under vacuum or liquid phase or mixed gas-liquid phase, depending on the volatility of the feedstock, but generally in the liquid phase.

Stoichiometric ratios or an excess of either olefin or linear polyaromatic compound can be used to form the adducts. The molar ratio of olefin to linear polyaromatic compound is preferably from 0.25:1 up to 10:1. Preferably, a molar excess of linear polyaromatic compounds is used to ensure a complete and large recovery of all olefins in the first and second adduction zone.

The residence time is for a time sufficient to adduct the desired amount of linear polyaromatic compound with the olefin. Typical residence times range from 30 minutes to 4 hours in a batch reaction.

An inert solvent can be utilized to dissolve the feedstock olefins or the linear polyaromatic compound or both in each of the adducting reactors. Preferred solvents are the hydrocarbon solvents which are liquid at reaction temperatures and in which the olefins, linear polyaromatic compound and olefin-linear polyaromatic compound adducts are soluble. Illustrative examples of useful solvents include the alkanes such as pentane, iso-pentane, hexane, heptane, octane, nonane, and the like; cycloalkanes such as cyclopentane, cyclohexane, and the like; and aromatics such as benzene, toluene, ethylbenzene, diethylbenzene, and the like. The amount of solvent to be employed can vary over a wide range without a deleterious effect on the reaction.

Preferably, the adducting reactions are carried out in the absence of a solvent, thereby improving the rate of reaction and avoid the need for additional equipment and process steps for separating the solvent.

After formation of the linear polyaromatic compound-olefin adduct in step a), the adduct stream flows to a separation vessel effective for separating the saturated hydrocarbons from the linear polyaromatic compound-olefin adduct to form a saturated hydrocarbon stream and an olefin adducted stream in step b). Due to the large molecular weight and structural difference between the adducts and the other ingredients in the reaction mixtures, such as saturated hydrocarbons and internal olefins, conventional separation techniques are quite suitable for removing the unreacted saturated hydrocarbons in step b) and internal olefins in step oiii) from the respective adducts. For example, the saturated hydrocarbons in step b) and the internal olefins in step oiii) may be removed at the overhead or in fractions, by partial vacuum or flash distillation of the reaction mixture to leave the adducts and unreacted linear polyaromatic compounds as a liquid bottoms. It is desirable to raise the temperature at the bottoms of the distillation column sufficient to retain the bottoms in liquid state, while keeping the temperature and residence time as low as possible to avoid dissociating the adducts. Suitable temperatures at the bottoms of the separation vessel range from 210° C. to 280° C., more preferably from 230° C. to 270° C. While the pressure is not particularly limited, and the separation can be conducted under atmospheric pressure, it is preferred to conduct the separation under slight vacuum, e.g. 200 mmHg to 700 mmHg, to reduce the operating temperature and the residence time within the separation vessel. The residence time within the vessel should be short to avoid excessive dissociation of the adducts, such as from 1 to 30 minutes.

In step b), the unreacted saturated hydrocarbon stream distillate includes paraffins and may include, if present in the feedstock composition, aromatics and oxygenates such as the alcohols, ketones, acids, along with internal and branched olefins which failed to adduct with the linear polyaromatic compound.

Alternatively, the adducts may be separated by cooling the reaction mixture until the adduct crystallizes out, followed by filtration or centrifugation to remove the unreacted saturated hydrocarbons in step b).

In most cases, any unreacted linear polyaromatic compound will separate out with the adduct in the adducted olefin stream and the adducted linear alpha olefin stream. Other ingredients, such as small amounts of higher molecular weight unreacted olefins, internal olefins, and branched olefins, may remain in the adducted olefin stream and the adducted linear alpha olefin stream.

The recovery of a stream in a separation operation is determined by the molar ratio of linear polyaromatic compound to olefins, the adducting residence time, the temperature within the separation vessel, and most importantly, the residence time (rate of separation) of the reaction mixture in the separation vessel. To obtain a large olefin composition recovery, any one or a combination of the following variables are adjusted: a high linear polyaromatic compound to olefin molar ratio, e.g., >1, long residence times to ensure complete adduction, and moderate distillation temperatures to avoid dissociating the adducts.

The rate of olefin recovery from the feedstock is not limited, and generally will depend upon the amount of olefin present in the feedstock. In one embodiment, the rate of recovery of olefin adducts from the first separation vessel, in moles/unit time, range from 0.10 to 0.40, more preferably from 0.15 to 0.35, each based upon a feedstock rate of 1.00. At these rates, from 40% to 100% of the olefins in the feedstock may be recovered into the olefin composition. In another embodiment, the rate of recovery ranges from 0.20 to 0.30, based upon a feedstock rate of 1.00.

In general, the recovery of olefins from the feedstock ranges from 70% to 100%.

The linear polyaromatic compound-olefin adducts in the adducted stream may be dissociated in a dissociation zone. The dissociation process can be accomplished by feeding the adducted olefin stream to a dissociation vessel where the adducted olefin stream is heated and pyrolyzed at a temperature of from about 200° to about 500° C., preferably from about 300° to about 350° C., for a time sufficient to dissociate the adducts. The dissociation temperature can be further reduced below 200° C. by stripping olefin gas as it is liberated using an inert gas. The pyrolysis frees the olefins from the linear polyaromatic compound. One or more dissociation vessels may be used in series to conduct the dissociation, and the dissociation vessels may also be operated under a partial vacuum up to superatmospheric pressures.

The linear polyaromatic compound may subsequently be separated from the resulting mixture by any conventional means, which may occur simultaneously with the pyrolysis operation, such as by vacuum or flash distilling off the olefins along with any impurities at the pyrolysis temperatures, and removing the linear polyaromatic compound as a bottoms from the dissociation zone. The dissociation vessel may be operated under slight vacuum to lower the boiling point of the dissociated linear alpha olefin and at a temperature sufficient to dissociate the adduct. Other separation techniques include filtration and centrifugation.

The olefin composition, whether separated or in mixture with the dissociated linear polyaromatic compounds, is now enriched in the concentration of olefins over the concentration of olefins feedstock. Likewise, when the saturated hydrocarbons are separated from the linear polyaromatic compound-olefin adduct in the separation vessel as a first saturated hydrocarbon stream, the first saturated hydrocarbon stream is enriched in its concentration of saturated hydrocarbons over the concentration of saturated hydrocarbons in the feedstock flowing to the first adduct reaction zone, and the concentration of olefins in the first saturated hydrocarbon stream is reduced over the concentration of olefins in the feedstock entering the first adduct reaction zone.

In the next step of the process, step si), the first saturated hydrocarbon stream comprising an enriched concentration of saturated hydrocarbons and a reduced concentration of linear alpha olefins and internal olefins, is contacted with linear polyaromatic compounds in a second adducting reaction zone under conditions effective to form a reaction mixture comprising second linear polyaromatic compound-olefin adducts and an second saturated hydrocarbon composition. Suitable reaction conditions and vessels include those used in the adducting reaction zone for the feedstock.

Once the second linear polyaromatic compound-linear alpha olefin adduct has been formed in the second reaction zone in step si), the adduct stream flows to a separation vessel in step sii) effective for separating the second linear polyaromatic compounds-olefin adducts from the saturated hydrocarbons to form an second saturated hydrocarbon stream enriched in the concentration of saturated hydrocarbons over the concentration of saturated hydrocarbons in the first saturated hydrocarbons stream, and a second linear polyaromatic compound-olefin adduct stream.

Suitable methods and conditions for separating the second adducts from the second reaction mixture include any of the methods used to remove the adducted olefins from the reaction mixture in the first separation zone. Preferably, the second reaction mixture is distilled and a second saturated hydrocarbon stream is removed at the overhead of the distillation column, while the olefin adducts are removed from the column as a liquid bottoms stream. The second saturated hydrocarbon stream includes some internal olefins and alpha olefins, but in reduced concentrations over the concentration of these species in the first saturated hydrocarbon stream. However, the concentration of the saturated hydrocarbons in the second saturated hydrocarbon stream is enriched over their concentration in the first saturated hydrocarbon stream.

The linear polyaromatic compound-olefin adducts in the olefin adduct stream removed from step sii) are dissociated in step siii) in a dissociation zone to form linear polyaromatic compounds and a second olefin composition. Suitable methods and conditions for dissociating the adducts in the linear alpha olefins adduct stream include the dissociation conditions effective for dissociating the olefins adducts formed removed in the first separation zone.

For purposes of measuring the percentage reduction of a species in a stream, the concentration (all concentrations determined on the basis of the total weight of all ingredients present in the stream in question) of the species or series of species in question contained in the product stream is subtracted from the concentration of the species or series of species in question contained in the predecessor stream in question, the difference then divided by the concentration of the same species in the predecessor stream multiplied by 100. For purposes of measuring the % enrichment of a species in a stream, the concentration of the species or series of species in the predecessor or feedstock stream is subtracted from the concentration of species or series of species in question contained in the product stream, the difference then divided by the concentration of those same species present in the predecessor feedstock stream and multiplied by 100. For purposes of adding together a series of species, the sum total of the series in the predecessor stream is added, and then the sum total of the species in the product stream are added if the concentration of the particular species is enriched over that particular species in the predecessor stream, and subtracted if the concentration of the particular species is reduced from the concentration in the predecessor stream. The total in the product stream is then compared to the total in the predecessor stream to determine whether the total of the series in the product stream was enriched or reduced over the sum total in the predecessor stream. The appropriate calculation mentioned above is then applied depending on whether the series in the product stream were reduced or enriched.

The Concentration of Species in the Olefin Composition and First Saturated Hydrocarbon Stream Relative to the Concentration of Species in the Feedstock In one embodiment, the concentration of all olefins in the first saturated hydrocarbon stream are reduced through the process of the invention by at least 15%, preferably at least 30%, more preferably at least 40%, over the concentration of all the olefins in the feedstock.

Since the linear polyaromatic compound is more selective towards adducting with linear alpha olefins relative to other olefins, the concentration of linear alpha olefins in the first saturated hydrocarbon stream in another embodiment are reduced by at least 30%, more preferably by at least 40%, most preferably by at least 50%, over the concentration of linear alpha olefins present in the feedstock stream.

The concentration of saturated hydrocarbon in the first saturated hydrocarbon stream is enriched over the concentration of saturated hydrocarbon in the feedstock stream. In an embodiment of the invention, the concentration is enriched by at least 5%, preferably by at least 10%, more preferably by at least 20%, and can be enriched by 100–400%, especially when the concentration of saturated hydrocarbon in the feedstock is low. Generally, the degree of enrichment of saturated hydrocarbon in the saturated hydrocarbon stream varies inversely with the concentration of the saturated hydrocarbons in the particular feedstock employed.

In another embodiment of the invention, the concentration of saturated hydrocarbons in the olefin composition is reduced through the process of the invention in only one pass by at least 80%, preferably by at least 90%, more preferably by at least 95% over the concentration of saturated hydrocarbon in the feedstock, and most preferably by 100%.

The concentration of linear alpha olefins in the olefin composition is enriched over the concentration of linear alpha olefins present in the feedstock stream. In an embodiment of the invention, the concentration of linear alpha olefins present in the olefin composition is enriched by at least 30%, more preferably by at least 40%, most preferably by at least 60%, over the concentration of linear alpha olefins present in the feedstock composition. The process of the invention can achieve concentrations of linear alpha olefin in the olefin composition higher than 80 wt. %, more preferably at least 90 wt. %.

Further, the concentration of all olefins in the olefin composition is enriched over the concentration of all olefins in the feedstock stream. The degree of olefin enrichment varies inversely with the concentration of olefins present in the feedstock. In a preferred aspect of this embodiment, the concentration of all olefins in the olefin composition is enriched by at least 40%, preferably by at least 60%.

The process of the invention is capable of separating olefins from saturated hydrocarbons in a feedstock consisting essentially of saturated hydrocarbons and olefins, resulting in a concentration of olefins in the olefin composition ranging from 90% to 100%.

Enrichment and Reduction of Species in the Second Saturated Hydrocarbon Stream and the Second Olefin Composition Relative to the First Saturated Hydrocarbon Stream And the Feedstock The process of the invention enriches the concentration of saturated hydrocarbons in the second saturated hydrocarbon stream relative to both the first saturated hydrocarbon stream and the feedstock. The degree of enrichment is preferably at least 5%, more preferably at least 10%. In general, the degree of enrichment will not be extremely high at this stage since the first adduction and separation highly concentrates the amount of saturated hydrocarbon in the first hydrocarbon stream.

The second olefin composition is enriched in linear alpha olefins over the concentration of linear alpha olefins in the first saturated hydrocarbon stream and in the feedstock, preferably by at least 50%, more preferably by at least 100%.

The concentration of internal olefins is also enriched in the second olefin composition over the concentration of internal olefins in the first saturated hydrocarbon stream, preferably by at least 20%, more preferably by at least 50%.

To further illustrate the invention, the FIGURE depicts a block flow diagram in which each of blocks 1 and 2 represent the adduction, separation, and dissociation steps, and lines 1,2,3,4, and 5 represent the feed and product streams into and from each block. Block 1 represents the first adduction zone, separation zone, and dissociation zone. Block 2 represents the second adduction zone, separation zone, and dissociation zone. Line 1 represents the composition of the feedstock, Line 2 represents the composition of the saturated hydrocarbon stream, Line 3 represents the olefin composition stream, Line 4 represents the second saturated hydrocarbon stream, and Line 5 represents the composition of the second olefin composition stream.

The modeled mass balances tabulated below illustrate one of the embodiments of the invention wherein the recovery of a high concentration of linear alpha olefins in the olefin composition, and recovery of internal olefins and alpha olefins from the first saturated hydrocarbon stream is desirable. Table A tabulates the mass balance based upon the quantity of each species in a feed and product stream, while Table B presents a mass balance based upon the concentration of each species in a feed and product stream. Table A results are reported as moles/unit time, and Table B results are reported as a mole percent composition in each stream. The mass balances are on a calculated basis to illustrate the concept of the invention, and are based upon the use of anthracene as the linear polyaromatic compound and upon the assumptions noted below Table B.

TABLE A

|  | 1 | 2 | 3 | 4 | 5 |
|---|---|---|---|---|---|
| Paraffins (linear/branched) | 0.15 | 0.15 | 0.00 | 0.15 | 0.00 |
| Saturated alkyl aromatics | 0.15 | 0.15 | 0.00 | 0.15 | 0.00 |
| Saturated oxygenates | 0.15 | 0.15 | 0.00 | 0.15 | 0.00 |
| Linear alpha olefins | 0.20 | 0.06 | 0.14 | 0.00 | 0.06 |
| Linear 2-olefins | 0.10 | 0.05 | 0.05 | 0.01 | 0.05 |
| 2-methyl 1-olefins | 0.25 | 0.22 | 0.03 | 0.11 | 0.11 |
| Total | 1.00 | 0.79 | 0.21 | 0.57 | 0.21 |

TABLE B

|  | 1 | 2 | 3 | 4 | 5 |
|---|---|---|---|---|---|
| Paraffins (linear/branched) | 15% | 19% | 0% | 26% | 0% |
| Saturated alkyl aromatics | 15% | 19% | 0% | 26% | 0% |
| Saturated oxygenates | 15% | 19% | 0% | 26% | 0% |
| Linear alpha olefins | 20% | 8% | 66% | 1% | 27% |

TABLE B-continued

|  | 1 | 2 | 3 | 4 | 5 |
|---|---|---|---|---|---|
| Linear 2-olefins | 10% | 7% | 22% | 1% | 22% |
| 2-methyl 1-olefins | 25% | 28% | 12% | 20% | 51% |

Assumptions:
Block 1 recovery set at 70% of the Linear Alpha Olefins. Block 2 recovery set at 63% of all the olefins in Stream 2. Equilibrium is assumed at each stage. Assume the equipment is capable of perfect rejection of saturated hydrocarbons, aromatics, and oxygenates. The ratio of equilibrium constants between linear alpha olefins and linear 2-olefins is set at 2.7. The ratio of equilibrium constants between linear alpha olefins and 2-Methyl 1-Olefins is set at 20. In block 1, the percentage of linear 2-olefin extracted from block 1 is 46%, and of the 2-methyl 1-olefin is 10%. In block 2, 88% of the linear 2-olefins are extracted, and 49% of the 2-methyl 1-olefin are extracted, each based upon the amount of material entering block 2.

The mass balances tabulated below illustrate another modeled embodiment of the invention wherein the recovery of higher quantities, albeit at lower concentrations relative to the embodiment above, of linear alpha olefins in the linear alpha olefin stream is desirable. Table C tabulates the mass balance based upon the quantity of each species in a feed and product stream, while Table D presents a mass balance based upon the concentration of each species in a feed and product stream. The mass balances are on a calculated basis to illustrate the concept of the invention, and are based upon the use of anthracene as the linear polyaromatic compound and upon the assumptions noted below Table D.

TABLE C

|  | 1 | 2 | 3 | 4 | 5 |
|---|---|---|---|---|---|
| Paraffins (linear/branched) | 0.15 | 0.15 | 0.00 | 0.15 | 0.00 |
| Saturated alkyl aromatics | 0.15 | 0.15 | 0.00 | 0.15 | 0.00 |
| Saturated oxygenates | 0.15 | 0.15 | 0.00 | 0.15 | 0.00 |
| Linear alpha olefins | 0.20 | 0.03 | 0.17 | 0.00 | 0.03 |
| Linear 2-olefins | 0.10 | 0.03 | 0.07 | 0.00 | 0.03 |
| 2-methyl 1-olefins | 0.25 | 0.19 | 0.06 | 0.10 | 0.09 |
| Total | 1.00 | 0.71 | 0.29 | 0.56 | 0.15 |

TABLE D

|  | 1 | 2 | 3 | 4 | 5 |
|---|---|---|---|---|---|
| Paraffins (linear/branched) | 15% | 21% | 0% | 27% | 0% |
| Saturated alkyl aromatics | 15% | 21% | 0% | 27% | 0% |
| Saturated oxygenates | 15% | 21% | 0% | 27% | 0% |
| Linear alpha olefins | 20% | 4% | 58% | 0% | 19% |
| Linear 2-olefins | 10% | 5% | 23% | 1% | 19% |
| 2-methyl 1-olefins | 25% | 28% | 19% | 18% | 63% |

Assumptions:
Block 1 recovery set at 85% of all the Linear Alpha Olefins. Block 2 recovery set at 59% of all the olefins in Stream 2. Equilibrium is assumed at each stage. Assume the equipment is capable of perfect rejection of saturated hydrocarbons, aromatics, and oxygenates. The ratio of equilibrium constants between linear alpha olefins and linear 2-olefins is set at 2.7. The ratio of equilibrium constants between linear alpha olefins and 2-Methyl 1-Olefins is set at 20. In block 1, the percentage of linear 2-olefin and 2-methyl 1-olefin extracted from block 1 is 68% and 22%, respectively. In block 2, the percentage of the linear 2-olefins and 2-methyl 1-olefin extracted are 88% and 49%, respectively, each based upon the amount of material entering block 2.

Fisher-Tropsch streams contain a variety of difficult to separate species, including saturated hydrocarbons, aromatics, oxygenates, internal olefins, branched olefins, and linear alpha olefins. An advantage of a Fisher-Tropsch stream is that it contains a mixture of both even and odd carbon, and the process of the invention produces a stream having even and odd carbon number olefin species with a very low to zero amount of saturated hydrocarbons and high concentrations of linear alpha olefins. The process of the invention can also provide a Fisher-Tropsch olefin composition having a mixture of internal olefins and/or branched olefins, and linear alpha olefins with low amounts of saturated hydrocarbons.

In one embodiment, the process of the invention provides a composition, preferably Fisher-Tropsch derived, comprising odd and even numbered olefins, an average carbon number ranging from $C_5$ to $C_{20}$, preferably $C_6$ to $C_{18}$, or optionally in the $C_6$ to $C_{12}$ range, comprising:

a) at least two linear alpha olefin species having different carbon chain lengths;

b) the two most predominant (on a mole basis) linear alpha olefin species of the at least two linear alpha olefin species are each within the range of $C_6$ to $C_{18}$, or in the case of using a $C_6$ to $C_{12}$ feedstock, within that range, inclusive;

c) the two most predominant linear alpha olefin species are present in an amount of at least 20 wt %, preferably at least 30 wt. %, more preferably at least 40 wt. %, based on the weight of the olefins in the composition;

d) cumulatively, the total amount of linear alpha olefins present in the composition within said range, inclusive, is at least 40 wt. %, preferably at least 60 wt. %, more preferably at least 70 wt. %, and even 90 wt. % or more, based on the weight of the olefins in the composition;

e) one or more odd numbered olefins within the range present in an amount of at least 10 wt. %, preferably at least 20 wt. %, more preferably at least 30 wt. %, and even 40 wt. % or more, cumulative;

f) a cumulative amount of aromatics, saturated hydrocarbons, and oxygenates of 10 wt. % or less, based on the weight of the composition; and preferably g) 6 wt. % or less of branched olefins having branching at the $C_2$ or $C_3$ position relative to the most proximate double bond, more preferably 4 wt. % or less, based on the weight of the composition.

In another embodiment of the invention, the above mentioned composition has as one of the two most predominant olefin species an odd carbon number linear alpha olefin.

In another embodiment of the invention, there is provided a composition, preferably Fisher-Tropsch derived, having an average carbon number ranging from $C_6$ to $C_{18}$ comprising at least two linear alpha olefin species having different carbon chain lengths within said range, inclusive, at least 50 wt. % of linear alpha olefins, where the composition has a most predominant olefin species represented by n carbon numbers, wherein the next most predominant olefin species has either n+1 or n−1 carbon numbers; and wherein said composition comprises 10 wt. % or less of saturated hydrocarbons; and preferably wherein said composition has branched olefins containing branching at the $C_2$ or $C_3$ positions, relative to the most proximate double bond, in an amount of 6 wt. %, more preferably 4 wt. % or less, based on the weight of the composition.

The process of the invention advantageously provides an olefin stream which is highly concentrated in olefins, wherein the concentration of olefins in the olefin composition may be at least 90% and up to 100% olefin purity in the olefin composition. The process of the invention also provides for the recovery of a second olefin composition from a first saturated hydrocarbon stream, which second olefin composition is enriched in both linear alpha olefins and internal olefins.

The olefin composition stream and the second olefin composition are useful as a component in drilling fluids, to react with elemental sulfur to make sulfurized products as extreme pressure agents in metal working fluids, as a co-monomers for the polymerization of polyethylene, as an intermediate in making polyalpha olefins (PAO) used as a lubricant, as a chlorination feed to make polychlorinated hydrocarbons in PVC applications, to react with hydrogen sulfides to make primary and secondary mercaptans as pharmaceutical intermediates and as additives to modify the properties of rubber, as solvents, and as a precursor for the manufacture of plasticizer alcohols and detergent range alcohols and surfactants, which may be derivatized into detergent range sulfates or alkoxysulfates for laundry liquids and powders, dishwashing powders and liquids, bar soap, shampoo, liquid hand soap, and hard surface cleaners.

The ranges and limitations provided in the instant specification and claims are those which are believed to particularly point out and distinctly claim the instant invention. It is, however, understood that other ranges and limitations that perform substantially the same function in substantially the same manner to obtain the same or substantially the same result are intended to be within the scope of the instant invention. The present invention will now be illustrated by means of the following illustrative embodiments and examples which are provided for illustration and are not to be construed as limiting the invention.

EXAMPLE 1

To illustrate the concept of the invention, a Fisher-Tropsch stream comprised of the composition set forth in Table 1 was used as a feedstock. The FT composition was derived by passing syngas over a FT catalyst and subsequently distilling products in the boiling point range of hexyl to undecyl hydrocarbons. This composition was used as the feed. Hydrocarbons in the $C_7$–$C_{10}$ were the most abundant.

0.14 moles of anthracene having a 95% purity and 62.5 g of the feedstock were placed in an autoclave. The total olefin content of the charged feed was about 0.15 moles (19.8 g), for an olefin/anthracene molar ratio of 1.1:1. The autoclave was sealed and then purged with nitrogen. The autoclave was heated to 255° C. for 5.6 hours to form the Diels-Alder adduct between the olefin and the anthracene. The autoclave contents were stirred during heating.

Once the reaction was complete, the autoclave was cooled to 20° C. The product mixture was transferred to a glass flask and the unreacted olefin, saturated hydrocarbons, and unreacted oxygenates were removed by distillation as Product A. The composition of Product A was determined by gas chromatographic analysis.

The material remaining in the flask consisted of some entrained saturated hydrocarbons, unreacted anthracene, and the anthracene-olefin adduct. The flask and its contents were then heated to a temperature ranging from 310–350° C. to dissociate the adduct to anthracene and Product B described in Table 1 below. Product B was separated and isolated from the anthracene by distillation. 9.2 g of Product B was recovered. The composition of Product B was determined by gas chromatographic analysis.

The results indicate that Product A is enriched in saturated hydrocarbons (alkanes) over the concentration of saturated hydrocarbons in the feedstock stream, by 24%. The concentration of alpha olefin in the Product A stream was reduced by 55% over the concentration of alpha olefin in the feedstock.

Product B is greatly enriched in alpha olefin content and overall olefin content over the concentration of alpha olefin and overall olefin content in the feedstock stream. Product B is enriched in alpha olefin content by 202%, and in overall olefin content, Product A was enriched by 197% ([(88.21+ 5.77)−(27.18+4.43)]/(27.18+4.43)×100).

Further, the concentration of saturated hydrocarbon (alkane)in Product B stream was greatly reduced; by 95%. The presence of saturated hydrocarbons in Product B is due to its incomplete removal upon distillation of the unreacted material from the adduct before the dissociation step.

TABLE 1

| | SEPARATION OF SATURATED HYDROCARBONS FROM OLEFINS | | | | | |
|---|---|---|---|---|---|---|
| COMPOSITION | TOTAL WEIGHT (g) | ALKANES (wt. %) | INTERNAL OLEFINS (wt. %) | ALPHA OLEFINS (w %) | OXYGENATES (wt. %) | UNKOWNS (wt. %) |
| Feedstock | 62.5 | 63.8 | 4.43 | 27.18 | 3.06 | 1.45 |
| Product A | 44.3 | 79.25 | 4.6 | 12.23 | 3.01 | 0.91 |
| Product B | 9.3 | 3.31 | 5.77 | 88.21 | 2.0 | 0.81 |

The concentration of saturated hydrocarbons in Product A stream was enhanced, and the concentration of internal olefins in the Product A stream was enhanced, by separating a portion of the internal olefin in Product A stream from the saturated hydrocarbons.

44.3 g of Product A containing 7.5 g (0.059 moles) of olefin was treated with 0.034 moles of anthracene for 6 hours at 255° C. in the equipment noted above. The molar ratio of olefin to anthracene was 1.7:1. 30.24 g of unreacted material was removed by distillation as Product C stream. The bottoms of the distillation column was thermally dissociated at 310–350° C. as described above. 1.67 g of the resulting Product D internal olefin stream was removed by distillation from the dissociated anthracene. Each of Product C and D were analyzed by gas chromatography. The results are reported in Table 2.

Product C, compared to the feedstock stream Product A, was enriched in alkanes by 6.8%. The concentration of internal olefin in Product C, compared to the feedstock Product A stream, was decreased by 25%.

Product D was enriched in internal olefins and in alpha olefins over the concentration of each olefin in the feedstock Product A stream. The internal olefin enrichment was about 98%, and the alpha olefin enrichment was about 570%.

TABLE 2

SEPARATION OF INTERNAL OLEFINS FROM SATURATED HYDROCARBONS

| COMPOSITION | TOTAL WEIGHT (g) | ALKANES (wt. %) | INTERNAL OLEFINS (wt. %) | ALPHA OLEFINS (w %) | OXYGENATES (wt. %) | UNKOWNS (wt. %) |
|---|---|---|---|---|---|---|
| Product A Feedstock | 44.3 | 79.25 | 4.6 | 12.23 | 3.01 | 0.91 |
| Product C | 30.24 | 85.04 | 6.03 | 6.54 | 1.63 | 0.76 |
| Product D | 1.67 | 6.80 | 9.11 | 82 | 1.26 | 0.83 |

What we claim is:

1. A process for contacting a linear polyaromatic compound with a feedstock composition comprising linear alpha olefins, internal olefins, and saturated hydrocarbons, separating the olefins from the saturated hydrocarbons in the feedstock composition to form an olefin composition and a saturated hydrocarbon stream, subsequently contacting a linear polyaromatic compound saturated hydrocarbon stream comprising linear alpha olefins and internal olefins, and separating the internal olefins and linear alpha olefins from the saturated hydrocarbons in the saturated hydrocarbon stream to form a second saturated hydrocarbon stream and a second olefin composition, whereby the concentration of each of internal olefins and linear alpha olefins in the second olefin composition is enriched over the concentration of each of internal olefins and linear alpha olefins in the feedstock and in the olefin composition.

2. The process of claim 1, wherein the average carbon number of the feedstock ranges from $C_5$–$C_{20}$ and wherein the predominant olefin species in the feedstock is within said range, inclusive.

3. The process of claim 2, wherein the average carbon number of the feedstock ranges from $C_6$–$C_{18}$ and wherein the predominant olefin species in the feedstock is within said range, inclusive.

4. The process of claim 3, wherein the linear polyaromatic compound comprises substituted or unsubstituted anthracene or benzanthranene.

5. A process for contacting a linear polyaromatic compound with a feedstock composition comprising a fischer tropsch stream, separating the olefins from saturated hydrocarbons in the feedstock composition to form an olefin composition and a saturated hydrocarbon stream, subsequently contacting a linear polyaromatic compound with the saturated hydrocarbon stream comprising linear alpha olefins and internal olefins, and separating the internal olefins and linear alpha olefins from the saturated hydrocarbons in the saturated hydrocarbon stream to form a second saturated hydrocarbon stream and a second olefin composition, whereby the concentration of each of internal olefins and linear alpha olefins in the second olefin composition is enriched over the concentration of each of internal olefins and linear alpha olefins in the feedstock and in the olefin composition.

6. The process of claim 5, wherein the feedstock comprises a single carbon cut composition.

7. The process of claim 1 wherein said feedstock composition is contacted with said linear polyaromatic compound at a temperature of from 150° to about 290° C.

8. The process of claim 1 wherein said feedstock composition is contacted with said linear polyaromatic compound at a temperature of from about 240° to about 265° C.

9. The process of claim 1 wherein said olefins in said feedstock composition are at a molar ratio to said linear polyaromatic compounds of from about 0.25:1 to about 10:1.

10. The process of claim 7 wherein said olefins in said feedstock composition are at a molar ratio to said linear polyaromatic compounds of from about 0.25:1 to about 10:1.

11. The process of claim 8 wherein said olefins in said feedstock composition are at a molar ratio to said linear polyaromatic compounds of from about 0.25:1 to about 10:1.

12. The process of claim 1 wherein linear polyaromatic compound-olefin adduct formed in said feedstock composition is dissociated by heating said linear polyaromatic compound-olefin adduct to a temperature ranging from about 200° C. to 500° C.

13. The process of claim 7 wherein linear polyaromatic compound-olefin adduct formed in said feedstock composition is dissociated by heating said linear polyaromatic compound-olefin adduct to a temperature ranging from about 200° C. to 500° C.

14. The process of claim 8 wherein linear polyaromatic compound-olefin adduct formed in said feedstock composition is dissociated by heating said linear polyaromatic compound-olefin adduct to a temperature ranging from about 200° C. to 500° C.

15. The process of claim 9 wherein linear polyaromatic compound-olefin adduct formed in said feedstock composition is dissociated by heating said linear polyaromatic compound-olefin adduct to a temperature ranging from about 200° C. to 500° C.

16. The process of claim 10 wherein linear polyaromatic compound-olefin adduct formed in said feedstock composition is dissociated by heating said linear polyaromatic compound-olefin adduct to a temperature ranging from about 200° C. to 500° C.

17. The process of claim 12 wherein linear polyaromatic compound-olefin adduct formed in said feedstock composition is dissociated by heating said linear polyaromatic compound-olefin adduct to a temperature ranging from about 200° C. to 500° C.

18. The process of claim 12 wherein said linear polyaromatic compound-olefin adduct is heated to a temperature ranging from about 300° C. to 350° C.

19. The process of claim 16 wherein said linear polyaromatic compound-olefin adduct is heated to a temperature ranging from about 300° C. to 350° C.

20. The process of claim 17 wherein said linear polyaromatic compound-olefin adduct is heated to a temperature ranging from about 300° C. to 350° C.

21. The process of claim 1 wherein said linear polyaromatic compound is separated from the olefin composition by vacuum or flash distillation.

22. The process of claim 12 wherein the linear polyaromatic compound is separated from the olefin composition by vacuum or flash distillation.

23. The process of claim 19 wherein the linear polyaromatic compound is separated from the olefin composition by vacuum or flash distillation.

24. The process of claim 20 wherein the linear polyaromatic compound is separated from the olefin composition by vacuum or flash distillation.

25. The process of claim 1 wherein the feedstock composition comprises from 15 wt. % to 70 wt. % olefin, based on the weight of all ingredients in the feedstock.

26. The process of claim 1 wherein the feedstock composition comprises from 15 wt. % to 65 wt. % linear alpha olefin, based on the weight of all ingredients in the feedstock.

27. The process of claim 1 wherein the feedstock composition comprises from 5 wt. % to 65 wt. %. paraffin, based on the weight of all ingredients in said feedstock composition.

28. The process of claim 1 wherein the amount of all olefins in the feedstock composition other than linear alpha olefins ranges from 5 wt. % to 45 wt. %, based on the weight of all ingredients in said feedstock composition.

29. The process of claim 1 wherein the amount of paraffin ranges from 65 to 99 wt. % of all ingredients in said feedstock composition.

30. The process of claim 1 wherein the average carbon number of said feedstock composition ranges from $C_5$–$C_{20}$ and wherein the predominant olefin species in said feedstock composition is within said range, inclusive.

31. The process of claim 1 wherein the average carbon number of said feedstock composition ranges from $C_6$–$C_{18}$ and wherein the predominant olefin species in said feedstock composition is within said range, inclusive.

32. The process of claim 1 wherein said linear polyaromatic compound has a greater selectivity for linear alpha olefin compounds over other olefins in an amount of greater than 2:1 by mole.

33. The process of claim 7 wherein said linear polyaromatic compound has a greater selectivity for linear alpha olefin compounds over other olefins in an amount of greater than 2:1 by mole.

34. The process of claim 8 wherein said linear polyaromatic compound has a greater selectivity for linear alpha olefin compounds over other olefins in an amount of greater than 2:1 by mole.

35. The process of claim 9 wherein said linear polyaromatic compound has a greater selectivity for linear alpha olefin compounds over other olefins in an amount of greater than 2:1 by mole.

36. The process of claim 10 wherein said linear polyaromatic compound has a greater selectivity for linear alpha olefin compounds over other olefins in an amount of greater than 2:1 by mole.

37. The process of claim 16 wherein said linear polyaromatic compound has a greater selectivity for linear alpha olefin compounds over other olefins in an amount of greater than 2:1 by mole.

38. The process of claim 1 wherein said linear polyaromatic compound is selected from the group consisting of substituted and unsubstituted anthracene and benzanthracene, wherein said substituted anthracene and benzanthracene comprise substitutents which are sufficiently inert and insufficiently large to interfere with formation of a Diels Alder adduct between said linear polyaromatic compound and olefins in said feedstock composition.

39. The process of claim 7 wherein said linear polyaromatic compound is selected from the group consisting of substituted and unsubstituted anthracene and benzanthracene, wherein said substituted anthracene and benzanthracene comprise substitutents which are sufficiently inert and insufficiently large to interfere with formation of a Diels Alder adduct between said linear polyaromatic compound and olefins in said feedstock composition.

40. The process of claim 8 wherein said linear polyaromatic compound is selected from the group consisting of substituted and unsubstituted anthracene and benzanthracene, wherein said substituted anthracene and benzanthracene comprises substitutents which are sufficiently inert and insufficiently large to interfere with formation of a Diels Alder adduct between said linear polyaromatic compound and olefins in said feedstock composition.

41. The process of claim 9 wherein said linear polyaromatic compound is selected from the group consisting of substituted and unsubstituted anthracene and benzanthracene, wherein said substituted anthracene and benzanthracene comprise substitutents which are sufficiently inert and insufficiently large to interfere with formation of a Diels Alder adduct between said linear polyaromatic compound and olefins in said feedstock composition.

42. The process of claim 10 wherein said linear polyaromatic compound is selected from the group consisting of substituted and unsubstituted anthracene and benzanthracene, wherein said substituted anthracene and benzanthracene comprise substitutents which are sufficiently inert and insufficiently large to interfere with formation of a Diels Alder adduct between said linear polyaromatic compound and olefins in said feedstock composition.

43. The process of claim 16 wherein said linear polyaromatic compound is selected from the group consisting of substituted and unsubstituted anthracene and benzanthracene, wherein said substituted anthracene and benzanthracene comprise substitutents which are sufficiently inert and insufficiently large to interfere with formation of a Diels Alder adduct between said linear polyaromatic compound and olefins in said feedstock composition.

44. The process of claim 1 wherein said linear polyaromatic compound comprises unsubstituted anthracene.

45. The process of claim 7 wherein said linear polyaromatic compound comprises unsubstituted anthracene.

46. The process of claim 8 wherein said linear polyaromatic compound comprises unsubstituted anthracene.

47. The process of claim 9 wherein said linear polyaromatic compound comprises unsubstituted anthracene.

48. The process of claim 10 wherein said linear polyaromatic compound comprises unsubstituted anthracene.

49. The process of claim 16 wherein said linear polyaromatic compound comprises unsubstituted anthracene.

50. The process of claim 1 wherein the rate of olefin recovery from said feedstock composition ranges from 0.10 to 0.4 moles/unit time based on a feed rate of 1.0 moles/unit time.

51. The process of claim 7 wherein the rate of olefin recovery from said feedstock composition ranges from 0.10 to 0.4 moles/unit time based on a feed rate of 1.0 moles/unit time.

52. The process of claim 8 wherein the rate of olefin recovery from said feedstock composition ranges from 0.10 to 0.4 moles/unit time based on a feed rate of 1.0 moles/unit time.

53. The process of claim 9 wherein the rate of olefin recovery from said feedstock composition ranges from 0.10 to 0.4 moles/unit time based on a feed rate of 1.0 moles/unit time.

54. The process of claim 10 wherein the rate of olefin recovery from said feedstock composition ranges from 0:10 to 0.4 moles/unit time based on a feed rate of 1.0 moles/unit time.

55. The process of claim 16 wherein the rate of olefin recovery from said feedstock composition ranges from 0.10 to 0.4 moles/unit time based on a feed rate of 1.0 moles/unit time.

56. The process of claim 1 wherein the recovery of olefins from the feedstock ranges from 40 to 100%.

57. The process of claim 7 wherein the recovery of olefins from the feedstock ranges from 40 to 100%.

58. The process of claim 8 wherein the recovery of olefins from the feedstock ranges from 40 to 100%.

59. The process of claim 9 wherein the recovery of olefins from the feedstock ranges from 40 to 100%.

60. The process of claim 10 wherein the recovery of olefins from the feedstock ranges from 40 to 100%.

61. The process of claim 16 wherein the recovery of olefins from the feedstock ranges from 40 to 100%.

62. The process of claim 1 wherein the second saturated hydrocarbon stream is enriched in saturated hydrocarbons by at least 10%.

63. The process of claim 1 wherein the concentration of linear alpha olefins in the saturated hydrocarbon stream is reduced in one pass by at least 40% over the concentration of linear alpha olefins present in said feedstock composition.

64. The process of claim 1 wherein said feedstock composition comprises a single carbon cut composition.

65. The process of claim 1 wherein said feedstock composition comprises a single cut $C_6$, $C_8$, $C_9$, $C_{10}$, $C_{11}$, $C_{12}$, $C_{14}$, or $C_{16}$ composition.

66. The process of claim 1 wherein the concentration of saturated hydrocarbons in said second saturated hydrocarbon stream is enriched by at least 5% relative to the concentration of saturated hydrocarbons in said feedstock composition.

67. The process of claim 1 wherein the concentration of internal olefins in said second saturated hydrocarbon stream is reduced by at least 20% relative to the concentration of saturated hydrocarbons in said feedstock composition.

68. The process of claim 1 wherein the concentration of internal olefins in said second olefin composition is enriched by at least 50% relative to the concentration of saturated hydrocarbons in said feedstock composition.

69. The process of claim 1 wherein the concentration of linear alpha olefins present in said second olefin composition is enriched by at least 100% relative to the concentration of saturated hydrocarbons in said feedstock composition.

70. The process of claim 5 wherein said feedstock composition is contacted with said linear polyaromatic compound at a temperature of from 150° to about 290° C.

71. The process of claim 5 wherein said feedstock composition is contacted with said linear polyaromatic compound at a temperature of from about 240° to about 265° C.

72. The process of claim 5 wherein said olefins in said feedstock composition are at a molar ratio to said linear polyaromatic compounds of from about 0.25:1 to about 10:1.

73. The process of claim 70 wherein said olefins in said feedstock composition are at a molar ratio to said linear polyaromatic compounds of from about 0.25:1 to about 10:1.

74. The process of claim 71 wherein said olefins in said feedstock composition are at a molar ratio to said linear polyaromatic compounds of from about 0.25:1 to about 10:1.

75. The process of claim 5 wherein linear polyaromatic compound-olefin adduct formed in said feedstock composition is dissociated by heating said linear polyaromatic compound-olefin adduct to a temperature ranging from about 200° C. to 500° C.

76. The process of claim 70 wherein linear polyaromatic compound-olefin adduct formed in said feedstock composition is dissociated by heating said linear polyaromatic compound-olefin adduct to a temperature ranging from about 200° C. to 500° C.

77. The process of claim 71 wherein linear polyaromatic compound-olefin adduct formed in said feedstock composition is dissociated by heating said linear polyaromatic compound-olefin adduct to a temperature ranging from about 200° C. to 500° C.

78. The process of claim 72 wherein linear polyaromatic compound-olefin adduct formed in said feedstock composition is dissociated by heating said linear polyaromatic compound-olefin adduct to a temperature ranging from about 200° C. to 500° C.

79. The process of claim 73 wherein linear polyaromatic compound-olefin adduct formed in said feedstock composition is dissociated by heating said linear polyaromatic compound-olefin adduct to a temperature ranging from about 200° C. to 500° C.

80. The process of claim 74 wherein linear polyaromatic compound-olefin adduct formed in said feedstock composition is dissociated by heating said linear polyaromatic compound-olefin adduct to a temperature ranging from about 200° C. to 500° C.

81. The process of claim 75 wherein said linear polyaromatic compound-olefin adduct is heated to a temperature ranging from about 300° C. to 350° C.

82. The process of claim 76 wherein said linear polyaromatic compound-olefin adduct is heated to a temperature ranging from about 300° C. to 350° C.

83. The process of claim 77 wherein said linear polyaromatic compound-olefin adduct is heated to a temperature ranging from about 300° C. to 350° C.

84. The process of claim 5 wherein said linear polyaromatic compound is separated from the olefin composition by vacuum or flash distillation.

85. The process of claim 79 wherein the linear polyaromatic compound is separated from the olefin composition by vacuum or flash distillation.

86. The process of claim 80 wherein the linear polyaromatic compound is separated from the olefin composition by vacuum or flash distillation.

87. The process of claim 83 wherein the linear polyaromatic compound is separated from the olefin composition by vacuum or distillation.

88. The process of claim 5 wherein said linear polyaromatic compound has a greater selectivity for linear alpha olefin compounds over other olefins in an amount of greater than 2:1 by mole.

89. The process of claim 70 wherein said linear polyaromatic compound has a greater selectivity for linear alpha olefin compounds over other olefins in an amount of greater than 2:1 by mole.

90. The process of claim 71 wherein said linear polyaromatic compound has a greater selectivity for linear alpha olefin compounds over other olefins an amount of greater than 2:1 by mole.

91. The process of claim 72 wherein said linear polyaromatic compound has a greater selectivity for linear alpha olefin compounds over other olefins in an amount of greater than 2:1 by mole.

92. The process of claim 73 wherein said linear polyaromatic compound has a greater selectivity for linear alpha olefin compounds over other olefins in an amount of greater than 2:1 by mole.

93. The process of claim 74 wherein said linear polyaromatic compound has a greater selectivity for linear alpha olefin compounds over other olefins in an amount of greater than 2:1 by mole.

94. The process of claim 70 wherein said linear polyaromatic compound is selected from the group consisting of substituted and unsubstituted anthracene and benzanthracene, wherein said substituted anthracene and benzanthracene comprise substitutents which are sufficiently inert and insufficiently large to interfere with formation of a Diels Alder adduct between said linear polyaromatic compound and olefins in said feedstock composition.

95. The process of claim 71 wherein said linear polyaromatic compound is selected from the group consisting of substituted and unsubstituted anthracene and benzanthracene, wherein said substituted anthracene and benzanthracene comprise substitutents which are sufficiently inert and insufficiently large to interfere with formation of a Diels Alder adduct between said linear polyaromatic compound and olefins in said feedstock composition.

96. The process of claim 72 wherein said linear polyaromatic compound is selected from the group consisting of substituted and unsubstituted anthracene and benzanthracene, wherein said substituted anthracene and benzanthracene comprise substitutents which are sufficiently inert and insufficiently large to interfere with formation of a Diels Alder adduct between said linear polyaromatic compound and olefins in said feedstock composition.

97. The process of claim 73 wherein said linear polyaromatic compound is selected from the group consisting of substituted and unsubstituted anthracene and benzanthracene, wherein said substituted anthracene and benzanthracene comprise substitutents which are sufficiently inert and insufficiently large to interfere with formation of a Diels Alder adduct between said linear polyaromatic compound and olefins in said feedstock composition.

98. The process of claim 74 wherein said linear polyaromatic compound is selected from the group consisting of substituted and unsubstituted anthracene and benzanthracene, wherein said substituted anthracene and benzanthracene comprise substitutents which are sufficiently inert and insufficiently large to interfere with formation of a Diels Alder adduct between said linear polyaromatic compound and olefins in said feedstock composition.

99. The process of claim 5 wherein said linear polyaromatic compound comprises unsubstituted anthracene.

100. The process of claim 70 wherein said linear polyaromatic compound comprises unsubstituted anthracene.

101. The process of claim 71 wherein said linear polyaromatic compound comprises unsubstituted anthracene.

102. The process of claim 72 wherein said linear polyaromatic compound comprises unsubstituted anthracene.

103. The process of claim 73 wherein said linear polyaromatic compound comprises unsubstituted anthracene.

104. The process of claim 74 wherein said linear polyaromatic compound comprises unsubstituted anthracene.

105. The process of claim 5 wherein the rate of olefin recovery from said feedstock composition ranges from 0.10 to 0.4 moles/unit time based on a feed rate of 1.0 moles/unit time.

106. The process of claim 70 wherein the rate of olefin recovery from said feedstock composition ranges from 0.10 to 0.4 moles/unit time based on a feed rate of 1.0 moles/unit time.

107. The process of claim 71 wherein the rate of olefin recovery from said feedstock composition ranges from 0.10 to 0.4 molels/unit time based on a feed rate of 1.0 moles/unit time.

108. The process of claim 72 wherein the rate of olefin recovery from said feedstock composition ranges from 0.10 to 0.4 moles/unit time based on a feed rate of 1.0 moles/unit time.

109. The process of claim 73 wherein the rate of olefin recovery from said feedstock composition ranges from 0.10 to 0.4 moles/unit time based on a feed rate of 1.0 moles/unit time.

110. The process of claim 74 wherein the rate of olefin recovery from said feedstock composition ranges from 0.10 to 0.4 moles/unit time based on a feed rate of 1.0 moles/unit time.

111. The process of claim 5 wherein the recovery of olefins from the feedstock ranges from 40 to 100%.

112. The process of claim 70 wherein the recovery of olefins from the feedstock ranges from 40 to 100%.

113. The process of claim 71 wherein the recovery of olefins from the feedstock ranges from 40 to 100%.

114. The process of claim 72 wherein the recovery of olefins from the feedstock ranges from 40 to 100%.

115. The process of claim 73 wherein the recovery of olefins from the feedstock ranges from 40 to 100%.

116. The process of claim 74 wherein the recovery of olefins from the feedstock ranges from 40 to 100%.

117. The process of claim 5 wherein the second saturated hydrocarbon stream is enriched in saturated hydrocarbons by at least 10%.

118. The process of claim 5 wherein the concentration of linear alpha olefins in the saturated hydrocarbon stream is reduced in one pass by at least 40% over the concentration of linear alpha olefins present in said feedstock composition.

119. The process of claim 5 wherein the concentration of saturated hydrocarbons in said second saturated hydrocarbon stream is enriched by at least 5% relative to the concentration of saturated hydrocarbons in said feedstock composition.

120. The process of claim 5 wherein the concentration of internal olefins in said second saturated hydrocarbon stream is reduced by at least 20% relative to the concentration of saturated hydrocarbons in said feedstock composition.

121. The process of claim 5 wherein the concentration of internal olefins in said second olefin composition is enriched by at least 50% relative to the concentration of saturated hydrocarbons in said feedstock composition.

122. The process of claim 5 wherein the concentration of linear alpha olefins present in said second olefin composition is enriched by at least 100% relative to the concentration of saturated hydrocarbons in said feed stock composition.

123. A process for treating a feedstock composition comprising:
contacting a linear polyaromatic compound with a feedstock composition comprising a Fischer Tropsch stream;
separating olefins from saturated hydrocarbons in said feedstock composition to form an olefin composition and a saturated hydrocarbon stream,
subsequently contacting the saturated hydrocarbon stream comprising linear alpha olefins and internal olefins with a linear polyaromatic compound selected from the group consisting of substituted and unsubstituted anthracene and benzanthracene, wherein said substituted anthracene and benzanthracene comprise substitutents which are sufficiently inert and insufficiently large to interfere with formation of a Diels Alder adduct between said linear polyaromatic compound and olefins in said feedstock composition; and
separating the internal olefins and linear alpha olefins from the saturated hydrocarbons in the saturated hydrocarbon stream to form a second saturated hydrocarbon stream and a second olefin composition;
whereby the concentration of each of internal olefins and linear alpha olefins in the second olefin composition is enriched over the concentration of each of internal olefins and linear alpha olefins in the feedstock and in the olefin composition.

124. The process of claim 123 wherein said linear polyaromatic compound comprises unsubstituted anthracene.

125. The process of claim 123 wherein said feedstock composition is contacted with said linear polyaromatic compound at a temperature of from 150° to about 290° C.

126. The process of claim 124 wherein said feedstock composition is contacted with said linear polyaromatic compound at a temperature of from 150° to about 290° C.

127. The process of claim 123 wherein said feedstock composition is contacted with said linear polyaromatic compound at a temperature of from about 240° to about 265° C.

128. The process of claim 123 wherein said olefins in said feedstock composition are at a molar ratio to said linear polyaromatic compounds of from about 0.25:1 to about 10:1.

129. The process of claim 124 wherein said olefins in said feedstock composition are at a molar ratio to said linear polyaromatic compounds of from about 0.25 to about 10:1.

130. The process of claim 126 wherein said olefins in said feedstock composition are at a molar ratio to said linear polyaromatic compounds of from about 0.25:1 to about 10:1.

131. The process of claim 123 wherein linear polyaromatic compound-olefin adduct formed in said feedstock composition is dissociated by heating said linear polyaromatic compound-olefin adduct to a temperature ranging from about 200° C. to 500° C.

132. The process of claim 124 wherein linear polyaromatic compound-olefin adduct formed in said feedstock composition is dissociated by heating said linear polyaromatic compound-olefin adduct to a temperature ranging from about 200° C. to 500° C.

133. The process of claim 125 wherein linear polyaromatic compound-olefin adduct formed in said feedstock composition is dissociated by heating said linear polyaromatic compound-olefin adduct to a temperature ranging from about 200° C. to 500° C.

134. The process of claim 126 wherein linear polyaromatic compound-olefin adduct formed in said feedstock composition is dissociated by heating said linear polyaromatic compound-olefin adduct to a temperature ranging from about 200° C. to 500° C.

135. The process of claim 123 wherein said linear polyaromatic compound-olefin adduct is heated to a temperature ranging from about 300° C. to 350° C.

136. The process of claim 123 wherein said linear polyaromatic compound is separated from the olefin composition by vacuum or flash distillation.

137. The process of claim 124 wherein the linear polyaromatic compound is separated from the olefin composition by vacuum or flash distillation.

138. The process of claim 125 wherein the linear polyaromatic compound is separated from the olefin composition by vacuum or flash distillation.

139. The process of claim 126 wherein the linear polyaromatic compound is separated from the olefin composition by vacuum or flash distillation.

140. The process of claim 123 wherein said linear polyaromatic compound has a greater selectivity for linear alpha olefin compounds over other olefins in an amount of greater than 2:1 by mole.

141. The process of claim 125 wherein said linear polyaromatic compound has a greater selectivity for linear alpha olefin compounds over other olefins in an amount of greater than 2:1 by mole.

142. The process of claim 127 wherein said linear polyaromatic compound has a greater selectivity for linear alpha olefin compounds over other olefins in an amount of greater than 2:1 by mole.

143. The process of claim 123 wherein the rate of olefin recovery from said feedstock composition ranges from 0.10 to 0.4 moles/unit time based on a feed rate of 1.0 moles/unit time.

144. The process of claim 123 wherein the recovery of olefins from the feedstock ranges from 40 to 100%.

145. The process of claim 123 wherein the second saturated hydrocarbon stream is enriched in saturated hydrocarbons by at least 10%.

146. The process of claim 123 wherein the concentration of linear alpha olefins in the saturated hydrocarbon stream is reduced in one pass by at least 40% over the concentration of linear alpha olefins present in said feedstock composition.

147. The process of claim 123 wherein the concentration of saturated hydrocarbons in said second saturated hydrocarbon stream is enriched by at least 5% relative to the concentration of saturated hydrocarbons in said feedstock composition.

148. The process of claim 123 wherein the concentration of internal olefins in said second saturated hydrocarbon stream is reduced by at least 20% relative to the concentration of saturated hydrocarbons in said feedstock composition.

149. The process of claim 123 wherein the concentration of internal olefins in said second olefin composition is enriched by at least 50% relative to the concentration of saturated hydrocarbons in said feedstock composition.

150. The process of claim 123 wherein the concentration of linear alpha olefins present in said second olefin composition is enriched by at least 100% relative to the concentration of saturated hydrocarbons in said feedstock composition.

* * * * *